US00PP16361P2

(12) United States Plant Patent
Miyazaki

(10) Patent No.: US PP16,361 P2
(45) Date of Patent: Mar. 21, 2006

(54) ***PHLOX* PLANT NAMED 'SUNPHLOPIN'**

(50) Latin Name: *Phlox drummondii*
Varietal Denomination: Sunphlopin

(75) Inventor: Kiyoshi Miyazaki, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 57 days.

(21) Appl. No.: 11/041,621

(22) Filed: Jan. 22, 2005

(51) Int. Cl.
*A01H 5/00* (2006.01)

(52) U.S. Cl. ..... Plt./320

(58) Field of Classification Search ..... Plt./320
See application file for complete search history.

*Primary Examiner*—Anne Marie Grunberg
(74) *Attorney, Agent, or Firm*—C. A. Whealy

(57) ABSTRACT

A new and distinct cultivar of *Phlox* plant named 'Sunphlopin', characterized by its upright and uniformly mounded plant habit; freely branching habit; dense and bushy growth habit; attractive red purple-colored flowers with darker red purple-colored centers; freely and continuous flowering habit; tolerance to high temperatures; and good garden performance.

1 Drawing Sheet

Botanical designation: *Phlox drummondii.*
Cultivar denomination: 'Sunphlopin'.

BACKGROUND OF THE INVENTION

The present Invention relates to a new and distinct cultivar of *Phlox* plant, botanically known as *Phlox drummondii*, and hereinafter referred to by the cultivar name Sunphlopin.

The new *Phlox* is a product of a planned breeding program conducted by the Inventor in Yokaichi, Shiga, Japan. The objective of the breeding program was to create new compact *Phlox* cultivars with attractive flower coloration.

The new *Phlox* originated from a cross-pollination made by the Inventor in 1996 in Yokaichi, Shiga, Japan of a proprietary selection of *Phlox drummondii* identified as code number 9PH-18a, not patented, as the female, or seed, parent with a proprietary selection of *Phlox drummondii* identified as code number 9PH-18b, not patented, as the male, or pollen, parent. The new *Phlox* was discovered and selected by the Inventor as a flowering plant within the progeny of the stated cross-pollination in a controlled environment in Yokaichi, Shiga, Japan.

Asexual reproduction of the new cultivar by terminal cuttings at Yokaichi, Shiga, Japan since October, 2000, has shown that the unique features of this new *Phlox* are stable and reproduced true to type in successive generations.

SUMMARY OF THE INVENTION

Plants of the cultivar Sunphlopin have not been observed under all possible environmental conditions. The phenotype may vary somewhat with variations in environment such as temperature and light level without, however, any variance in genotype.

The following traits have been repeatedly observed and are determined to be the unique characteristics of 'Sunphlopin'. These characteristics in combination distinguish 'Sunphlopin' as a new and distinct cultivar of *Phlox:*

1. Upright and uniformly mounded plant habit.
2. Freely branching habit; dense and bushy growth habit.

3. Attractive red purple-colored flowers with darker red purple-colored centers.
4. Freely and continuous flowering habit.
5. Tolerant to high temperatures.
6. Good garden performance.

Plants of the new *Phlox* can be compared to plants of the parent selections. In side-by-side comparisons conducted in Yokaichi, Shiga, Japan, plants of the new *Phlox* differed from plants of the parent selections in the following characteristics:

1. Plants of the new *Phlox* were more compact than plants of the parent selections.
2. Plants of the new *Phlox* and the parent selections differed in stem and flower coloration.
3. Plants of the new *Phlox* had shorter sepals than plants of the parent selections.

Plants of the new *Phlox* can be compared to the *Phlox drummondii* cultivar Parona Rose with Eye, not patented. In side-by-side comparisons conducted in Yokaichi, Shiga, Japan, plants of the new *Phlox* differed from plants of the cultivar Parona Rose with Eye in the following characteristics:

1. Plants of the new *Phlox* were more compact and had shorter internodes than plants of the cultivar Parona Rose with Eye.
2. Plants of the new *Phlox* were more freely branching than plants of the cultivar Parona Rose with Eye.
3. Plants of the new *Phlox* had smaller leaves than plants of the cultivar Parona Rose with Eye.
4. Plants of the new *Phlox* were more freely flowering than plants of the cultivar Parona Rose with Eye.
5. Plants of the new *Phlox* flowered from April to late October whereas plants of the cultivar Parona Rose with Eye flowered from April to June.
6. Plants of the new *Phlox* and the cultivar Parona Rose with Eye differed in flower color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new *Phlox*.

The photograph at the top of the sheet is a side perspective view of a typical plant of 'Sunphlopin'.

The photograph at the bottom of the sheet is a close-up view of typical flowers and leaves of 'Sunphlopin'.

DETAILED BOTANICAL DESCRIPTION

The aforementioned photographs, following observations and measurements describe plants grown in Yokaichi, Shiga, Japan in an outdoor nursery and under commercial production practices during the summer. Plants were grown in 15-cm containers and were about five months old when the photographs and description were taken. During the production of the plants, day temperatures averaged 25° C. and night temperatures averaged 15° C. Plants were pinched one time in the spring. In the following description, color references are made to The Royal Horticultural Society Colour Chart, 2001 Edition, except where general terms of ordinary dictionary significance are used.

Botanical classification: *Phlox drummondii* cultivar Sunphlopin.

Parentage:

*Female, or seed, parent.*—Proprietary selection of *Phlox drummondii* identified as code number '9PH-18a', not patented.

*Male, or pollen, parent.*—Proprietary selection of *Phlox drummondii* identified as code number '9PH-18b', not patented.

Propagation:

*Type.*—By terminal cuttings.

*Time to initiate roots.*—About two to three weeks at 20 to 25° C.

*Time to produce a rooted plant.*—About one to two months at 20 to 25° C.

*Root description.*—Fine, fibrous, fleshy; ivory to pale brown in color.

*Rooting habit.*—Freely branching.

Plant description:

*Plant form/habit.*—Upright and uniformly mounded plant habit; broadly inverted triangle; vigorous growth habit. Freely branching habit with short internodes, dense and bushy growth habit.

*Plant height.*—About 14.6 cm.

*Plant width* (*spread*).—About 21.5 cm.

*Lateral branches.*—Length: About 10 cm. Diameter: About 1.7 mm. Internode length: About 1.3 cm. Strength: Strong. Texture: Pubescent. Color: 146C.

*Foliage description.*—Arrangement: Alternate, simple; sessile. Length: About 3.2 cm. Width: About 1.2 cm. Shape:Lanceolate. Apex: Acute. Base: Cordate. Margin: Entire. Texture, upper and lower surfaces: Pubescent. Venation pattern: Pinnate; reticulate. Color: Developing and fully expanded leaves, upper surface: 146A; venation, 146A. Developing and fully expanded leaves, lower surface: 147B; venation, 147B.

Flower description:

*Flower type/habit.*—Single, rounded salverform flowers arranged in terminal and lateral cymes; flowers face upright and outward. Freely flowering habit with about six flowers per inflorescence.

*Fragrance.*—Present; typical of *Phlox*.

*Natural flowering season.*—Continuously flowering from April to late October in Japan. Flowers not persistent.

*Postproduction longevity.*—Flowers last about five days on the plant.

*Inflorescence height.*—About 3.4 cm.

*Inflorescence diameter.*—About 5.6 cm.

*Flower buds.*—Height: About 1.2 cm. Diameter: About 2.3 mm. Shape: Clavate. Color: 65C.

*Flowers.*—Diameter: About 2.8 cm. Depth: About 1.5 cm.

*Petals.*—Quantity per flower: Typically five in a single whorl; petals fused at the base into a narrow tube. Lobe length: About 1.2 cm. Lobe width: About 1.5 cm. Shape: Broadly rhombic. Apex: Cuspidate. Margin: Entire. Aspect: Mostly flat. Texture, upper and lower surfaces: Smooth, glabrous. Color: Developing and fully expanded petals, upper surface: 61D; towards base, 61B. Developing and fully expanded petals, lower surface: 65C.

*Sepals.*—Quantity per flower: Typically five in a single whorl, fused; narrow tubular calyx. Length: About 5.3 mm. Width: About 0.9 mm. Shape: Lanceolate. Apex: Acute. Texture, upper and lower surfaces: Smooth, glabrous. Color, upper and lower surfaces: 137A.

*Pedicels.*—Length: About 1.1 cm. Diameter: About 0.7 mm. Texture: Pubescent. Color: 143C.

*Reproductive organs.*—Stamens: Quantity per flower: Typically five. Anther shape: Linear. Anther length: About 1 mm. Anther color: 9A. Pollen amount: Moderate. Pollen color: 13A. Pistils: Quantity per flower: Typically one. Stigma shape: Tri-parted. Stigma color: 1C. Style length: About 1 cm. Style color: N144B. Ovary color: 144B.

*Seed/fruit.*—Seed and fruit development have not been observed.

Disease/pest resistance: Plants of the new *Phlox* have not been noted to be resistant to specific pathogens and pests common to *Phlox*.

Garden performance: Plants of the new *Phlox* have been observed to have good garden performance and tolerate rain, wind and tolerated temperatures from 0 to 35° C.

It is claimed:

1. A new and distinct cultivar of *Phlox* plant named 'Sunphlopin', as illustrated and described.

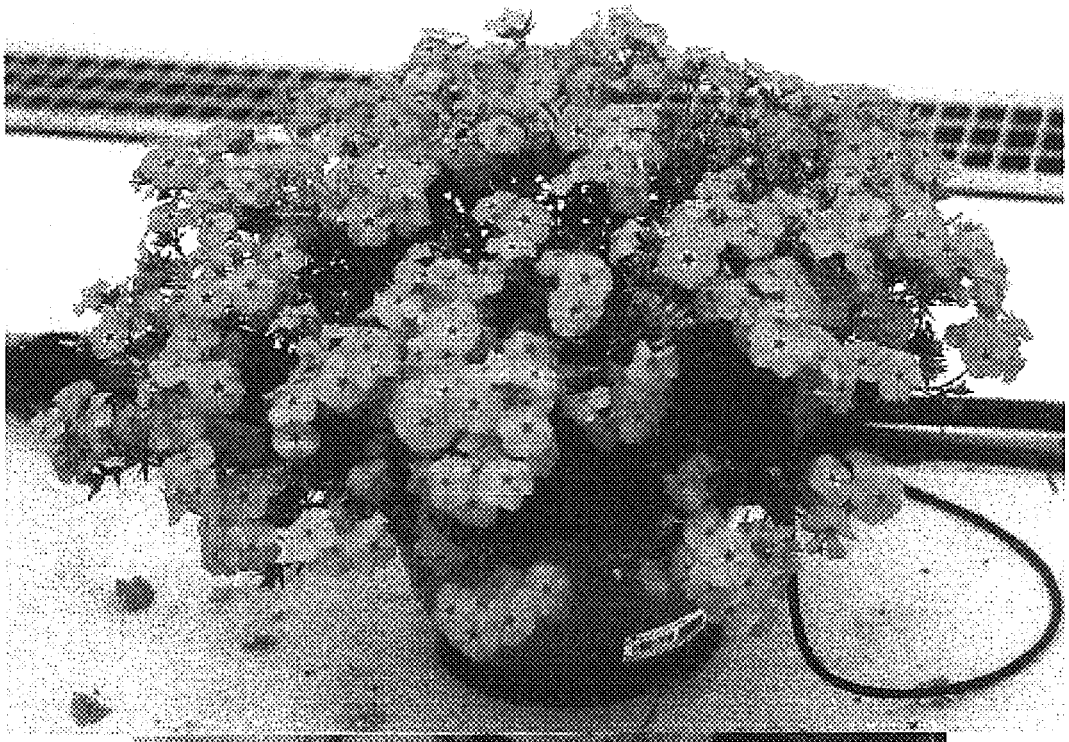
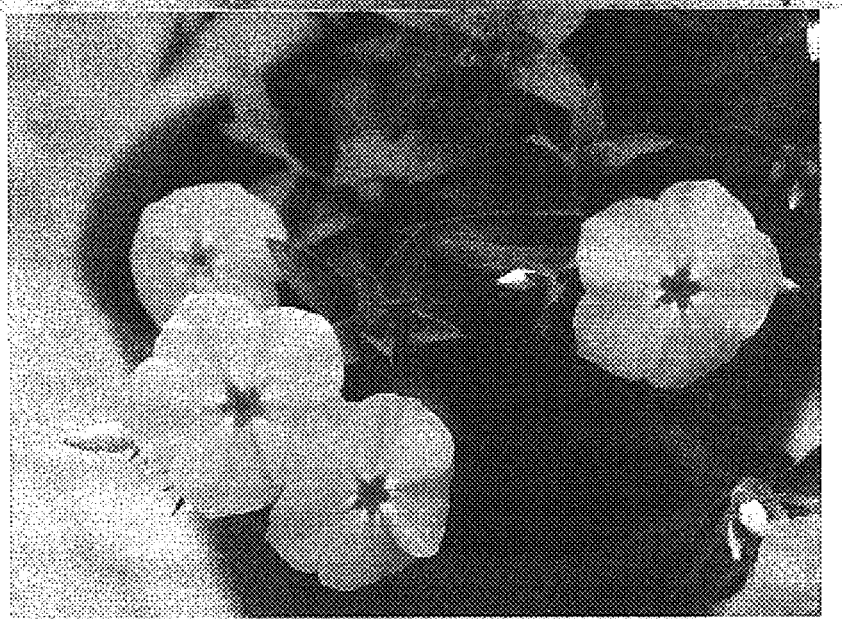

* * * * *